United States Patent [19]

Kocsis et al.

[11] 4,115,566
[45] Sep. 19, 1978

[54] 7α UREIDO CEPHEM-4-CARBOXYLIC ACID DERIVATIVES

[75] Inventors: Karoly Kocsis, Basel; Bruno Fechtig, Reinach; Hans Bickel, Binningen, all of Switzerland

[73] Assignee: Ciba-Geigy Corporation, Ardsley, N.Y.

[21] Appl. No.: 642,505

[22] Filed: Dec. 19, 1975

Related U.S. Application Data

[62] Division of Ser. No. 344,004, Mar. 22, 1973, Pat. No. 3,954,802.

[30] Foreign Application Priority Data

Mar. 29, 1972 [CH] Switzerland ............... 4732/72

[51] Int. Cl.² .................. A61K 31/545; C07D 501/28
[52] U.S. Cl. .................................... 424/246; 544/22; 544/28; 544/30
[58] Field of Search .................. 260/243 C; 424/246; 544/22, 28, 30

[56] References Cited

U.S. PATENT DOCUMENTS

| | | | |
|---|---|---|---|
| 3,687,949 | 8/1972 | Holdrege | 424/246 |
| 3,925,368 | 12/1975 | Cooper et al. | 260/243 C |
| 4,015,000 | 3/1977 | Kocsis et al. | 544/30 |

Primary Examiner—Donald G. Daus
Assistant Examiner—David E. Wheeler
Attorney, Agent, or Firm—John J. Maitner

[57] ABSTRACT

6-Acylamino-penam-3-carboxylic acids and 7-acylamino-3-cephem-4-carboxylic acids in which the acyl group has the formula

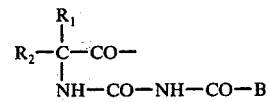

in which $R_1$ is hydrogen, $R_2$ is optionally substituted phenyl, thienyl or furyl, or $R_1$ and $R_2$ together are optionally substituted cycloalkyl, and B is a radical which is bonded via a sulphur atom or is bonded to oxygen or sulphur with the interposition of an optionally substituted $CH_2$-group.

7 Claims, No Drawings

7α UREIDO CEPHEM-4-CARBOXYLIC ACID DERIVATIVES

This is a division, of application Ser. No. 344,004, filed Mar. 22, 1973 now U.S. Pat. No. 3,954,802.

The invention relates to new therapeutically valuable derivatives of 6-amino-2,2-dimethyl-penam-3-carboxylic acid and of 7-amino-ceph-3-em-4-carboxylic acid and their salts, processes for their manufacture and pharmaceutical preparations which contain the new compounds.

The new compounds have the general formula I

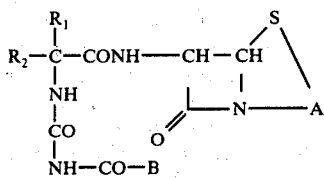

wherein the grouping -S-A- represents a radical of the formula Ia or Ib

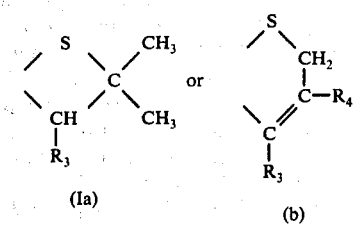

wherein $R_3$ denotes an optionally protected carboxyl group and $R_4$ represents hydrogen or an optionally substituted methyl group and wherein, if the radicals $R_1$ and $R_2$ are separate, $R_1$ is hydrogen and $R_2$ is optionally substituted phenyl, thienyl or furyl, and if the radicals $R_1$ and $R_2$ are linked, they form, together with the carbon atom, an optionally substituted cycloalkyl ring of 4 to 7 carbon atoms, and wherein B represents a radical with at most 20, above all at most 10, carbon atoms which is bonded via a sulphur atom or is bonded to oxygen or sulphur with the interposition of an optionally substituted $CH_2$ group.

Substituents of the abovementioned cyclic radicals $R_2$ or $R_1 + R_2$ are, for example, lower alkyl such as methyl, lower alkoxy such as methoxy, halogen atoms, for example fluorine or chlorine, trifluoromethyl, the nitro group and above all carbamoyl and acyl, especially lower alkanoyl such as acetyl, acylamino, especially lower alkanoylamino and lower alkoxycarbonylamino, for example acetylamino, tert.butoxycarbonylamino, di-lower alkylamino, for example dimethylamino, lower alkanoyloxy such as acetoxy and lower alkoxycarbonyl, such as methoxycarbonyl. The cyclic radicals are preferably unsubstituted. $R_1$ and $R_2$ together with the carbon atom represent above all cyclopentyl or cyclohexyl. If $R_2$ represents thienyl or furyl, these radicals are bonded in the 2- or 3-position, preferably in the 2-position.

Above all, $R_1$ represents hydrogen and $R_2$ represents unsubstituted phenyl.

B denotes a radical of the general formula Ic

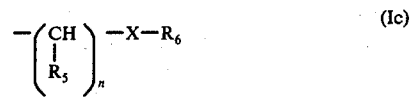

wherein $n = 0$ or 1 and X represents sulphur if $n = 0$, or represents carbonyloxy (—CO—O—) or sulphonyl ($SO_2$) if $n = 1$, and wherein $R_6$ represents an organic radical and $R_5$ represents hydrogen or an organic radical. If $n = 1$, B therefore represents

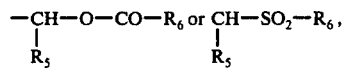

wherein $R_5$ and $R_6$ have the indicated meaning.

An organic radical $R_6$ is an optically substituted aliphatic, cycloaliphatic, cycloaliphatic-aliphatic, aromatic or araliphatic hydrocarbon radical or a heterocyclic or heterocyclic-aliphatic radical.

An aliphatic hydrocarbon radical $R_6$ is above all a lower alkyl radical, especially a radical with 1–4 carbon atoms such as methyl, ethyl, propyl, isopropyl, n-butyl and tert.butyl. Such a radical is preferably unsubstituted but can also be substituted by one or more substituents.

As substituents there are to be mentioned free, esterified or etherified hydroxyl or mercapto groups such as halogen (with an atomic weight of at most 127), especially chlorine or fluorine, acyloxy, above all lower alkanoyloxy such as acetoxy or aroyloxy such as benzoyloxy, lower alkoxy such as methoxy, aryloxy such as phenoxy which is optionally substituted, especially by halogen, nitro, lower alkyl or lower alkoxy, for example p-chlorophenoxy, lower alkylmercapto such as methylmercapto, and also trifluoromethyl, free or functionally modified carboxyl groups, for example ester groups, especially lower alkoxycarbonyl such as methoxycarbonyl, nitrile, optionally substituted carbamoyl, for example N-lower alkylcarbamoyl such as N-methylcarbamoyl, the nitro group and acyl groups, especially acyl of carboxylic acids, for example lower alkanoyl such as acetyl or monocyclic aroyl such as benzoyl.

A cycloaliphatic hydrocarbon radical $R_6$ is, for example, a cycloalkyl or cycloalkenyl radical with 3–8, preferably 5–6, carbon atoms, for example cyclohexyl and cyclohexenyl; a cycloaliphatic-aliphatic hydrocarbon radical is, for example, a cycloalkyl- or cycloalkenyl-lower alkyl radical, wherein cycloalkyl, cycloalkenyl and lower alkyl have the indicated meanings, for example cyclopentylmethyl and cyclohexenylmethyl. These radicals can be substituted in the same manner as the aliphatic hydrocarbon radicals described above; they can also possess lower alkyl groups, for example methyl, ethyl or tert.-butyl, as substituents.

An aromatic radical $R_6$ is a monocyclic or bicyclic radical, for example naphthyl and preferably phenyl. These radicals can be substituted in the same manner as the cyclic aliphatic radicals. Substituents are preferably halogen, above all chlorine, nitro, lower alkyl and lower alkoxy.

Aliphatic radicals $R_6$ can also be monocyclic or bicyclic. Above all, they are phenyl-lower alkyl radicals such as benzyl or phenylethyl. These radicals, also, can carry the substituents indicated above for the aliphatic cyclic radicals, and especially the substituents preferred for aromatic radicals.

Heterocyclic radicals $R_6$ are monocyclic or bicyclic radicals which contain nitrogen, sulphur and/or oxygen as hetero-atoms. They possess 5–8, preferably 5–6, ring members per ring. They can be saturated or unsaturated. Preferably, they are of aromatic character. They possess 1–4, preferably 1–2, hetero-atoms, above all one hetero-atom. They can possess a fused benzene ring. As examples there should be mentioned: furyl, thienyl, pyrryl, indolyl, oxazolyl, thiazolyl, imidazolyl, pyrazolyl, triazolyl, tetrazolyl, thiadiazolyl, thiazolidinyl, tetrahydrofuranyl, pyrrolidyl, pyridyl, quinolyl, isoquinolyl, tetrahydropyranyl, pyrimidyl, pyridazinyl, pyrazinyl, triazinyl, tetrazinyl, piperidyl, morpholinyl and thiamorpholinyl. The rings can possess substituents, as indicated above for the cycloaliphatic rings.

Heterocyclyl-aliphatic radicals $R_6$ are above all heterocyclyl-lower alkyl radicals, for example heterocyclyl-methyl radicals. Therein, the heterocyclyl radical is a radical such as described above. These radicals can also carry the substituents indicated above for cycloaliphatic radicals.

$R_5$ in the above formula Ic denotes, as already mentioned, hydrogen or an organic radical. The organic radical can have the same meaning as indicated for $R_6$. $R_5$ and $R_6$ can be identical or different. Preferably, $R_5$ represents hydrogen, lower alkyl, above all methyl, phenyl or 5–6-membered heterocyclyl with one hetero-atom, for example thienyl, furyl and pyridyl.

The substituent $R_3$ present in the penicillanic acid derivatives and cephalosporanic acid derivatives of the formulae Ia and Ib is, as has been mentioned, a free or protected carboxyl group. By a protected carboxyl group there is here to be understood a functionally modified carboxyl group, such as an esterified or amidised carboxyl group, or a carboxyl group present in the anhydride form.

An esterified carboxyl group $R_3$ is preferably a group which can be split easily, for example a group which can be split, if necessary in an acid or weakly alkaline medium, solvolytically, for example by hydrolysis or alcoholysis, hydrogenolytically, reductively, by nucleophilic exchange, photolytically or enzymatically, to give the free carboxyl group.

Ester groups which can easily be split by solvolysis with a solvent containing hydroxyl groups, for example water or alcohols such as, for example, methanol or ethanol, preferably under neutral conditions, are above all those which are derived from silyl, germanyl, plumbyl or stannyl alcohol. Such groups are described, for example, in British patent specification No. 1,073,530, in Netherlands published specification No. 67/17,107 and in German Offenlegungsschrift No. 1,800,698. In particular, groups of the formula $R_7R_8R_9$ Si—OCO— or $R_7R_8R_9$Sn—OCO— can be used, wherein $R_7$, $R_8$ and R are identical or different and represent alkyl, especially lower alkyl, aryl, for example phenyl, or aralkyl such as phenyl-lower alkyl, such as benzyl.

Esters which are split easily in an acid medium, for example in the presence of hydrogen chloride, hydrogen fluoride or hydrogen bromide, or of organic acids such as acetic acid, trifluoroacetic acid, formic acid or their mixtures with water, are above all those which are derived from lower alkanols which are poly-branched in the α-position or lower alkanols which contain, in the α-position, one or more electron donors such as optionally substituted aromatic hydrocarbon radicals or heterocyclyl radicals of aromatic character, such as phenyl, furyl or thienyl or aroyl radicals such as benzoyl or acyloxy radicals such as aroyloxy or lower alkanoyloxy. Such ester groups are, for example tert. butoxycarbonyl, tert. amyloxycarbonyl, cyclopentyloxycarbonyl, cyclohexyloxycarbonyl, adamantyloxycarbonyl, furfuryloxycarbonyl, 2-tetrahydrofuryloxycarbonyl, 2-tetrahydropyranyloxycarbonyl, benzyloxycarbonyl, p-nitrobenzyloxycarbonyl, p-methoxy-benzyloxycarbonyl, α-methyl-α-biphenylyl-methoxycarbonyl, 3,4-dimethoxybenzyloxycarbonyl, 3,5-dimethoxybenzyloxycarbonyl, diphenylmethoxycarbonyl, di(p-methoxyphenyl)-methoxycarbonyl, triphenylmethoxycarbonyl, benzoylmethoxycarbonyl, benzoyloxymethoxycarbonyl, acetoxymethylcarbonyl and pivaloyloxymethoxycarbonyl.

Ester groups which can be split hydrolytically under weakly basic or acid conditions are, for example, activated esters which are derived from optionally substituted phenol or benzyl alcohol, such as 4-nitrophenyl, 2,4-dinitrophenyl, 4-nitrobenzyl, 2,4,6-trichlorophenyl, and 2,3,4,5,6-pentachlorophenyl esters, and also, for example, phthaliminomethyl, succiniminomethyl, triphenylmethyl and bis-(4-methoxyphenoxy)-methyl esters.

Examples of ester groups which can be split by hydrogenolysis are those derived from optionally substituted benzyl alcohol, for example p-nitrobenzyl alcohol. Ester groups which can be split reductively without the conjoint use of catalysts, for example by treatment with nascent hydrogen, or by electrolytic reduction, are of greater importance. Such groups are derived, above all, from 2-halogeno-lower alkanols, for example from 2,2,2-trichloroethanol, 2-chloroethanol, 2-bromoethanol and 2-iodoethanol and also, for example, from benzoylmethanol or 4-pyridylmethanol. These alcohol groups can be removed by treatment with chemical reducing agents, preferably under neutral or weakly acid conditions, for example with zinc in the presence of aqueous acetic acid or formic acid or zinc in a lower alkanol or in pyridine, or by means of chromium-(II) reagents. The 4-pyridylmethoxy group is appropriately removed by electrolytic reduction.

Ester groups which can easily be split off photolytically, especially by irradiation with ultraviolet light, preferably under neutral or acid conditions, are derived from methanols containing one or two aryl radicals which are substituted, for example, by lower alkoxy groups especially methoxy and/or nitro groups. Such groups are above all 3-methoxy- and 4-methoxy-benzyloxycarbonyl, 3,4-dimethoxy- and 3,5-dimethoxybenzyloxycarbonyl, 2-nitrobenzyloxycarbonyl, 4,5-dimethoxy-2-nitrobenzyloxycarbonyl, α-phenyl-α-(3,4-dimethoxy-6-nitro-phenyl)-methoxycarbonyl and α-methyl-α-(3,4-dimethoxy-6-nitrophenyl)-methoxycarbonyl.

Esters which can be split enzymatically are above all those which contain an ester group which can be split under physiological conditions. These esters can be resorbed well in the organism and are therefore therapeutically usable as such. Esters of this nature are described, for example, in British patent specification No. 1,229,453 and in German patent application DT No. 1,951,012. The esters are derived from alcohols of the formula HO—CH₂OCO—OCO—$R_3''$, wherein $R_3''$ can represent a hydrogen atom, an alkyl radical, a cycloalkyl radical, a cycloalkylalkyl radical, an aryl radical, an aralkyl radical or a heterocyclyl radical. In particular, $R_3''$ can represent a lower alkyl radical with at most 5 carbon atoms such as methyl, ethyl, propyl, isopropyl, butyl, isobutyl and above all tert.-butyl, and also a monocyclic cycloalkyl radical with 3 to 7 carbon atoms; a bicyclic cycloalkyl radical, such as a 1-bicyclo-(2,2,2)-octyl or adamantyl radical; a monocyclic aryl radical, for example an optionally substituted phenyl radical; a bicyclic aryl radical, such as a 1-naphthyl radical, a 2-naphthyl radical or a substituted naphthyl radical; a monocyclic or bicyclic aralkyl radical, for example a benzyl or phenylethyl radical or a naphthyllower alkyl radical, such as naphthylmethyl. $R_3''$ can also represent a heterocyclyl radical with 5–6 ring atoms and at least one nitrogen, sulphur or oxygen atom, for example thienyl, furyl, pyrryl, oxazolyl, thiazolyl and imidazolyl.

Examples of substituents in the above ring systems which form a part of $R_3$ are, inter alia, lower alkyl radicals, lower alkoxy radicals, lower alkylmercapto radicals, lower halogenalkyl radicals, such as monohalogenoalkyl, dihalogenoalkyl or trihalogenoalkyl radicals, in which the halogen can be fluorine, chlorine or bromine, and nitro groups. Processes for the manufacture of the above esters are described in the British Patent Specification and German Application which have been mentioned.

The carboxyl group $R_3$ can also be esterified by a lower alkanol such as methanol or ethanol.

In the amidised carboxyl group $R_3$ the amide nitrogen atom can optionally be substituted, for example by monovalent or bivalent aliphatic hydrocarbon radicals which can optionally be interrupted by oxygen, nitrogen or sulphur atoms. Such radicals are above all lower alkyl, for example as mentioned above, especially methyl, or lower alkylene, for example 1,4-butylene or 1,5-pentylene, oxa-lower alkylene, for example 3-oxa-1,5-pentylene, or aza-lower alkylene, for example 3-methyl-3-aza-1,5-pentylene.

A protected carboxyl group $R_3$ present in the anhydride form, preferably in the form of a mixed anhydride, is above all a group which can be split hydrolytically. The second acyl radical is, for example, the acyl radical of a carboxylic acid, especially of a lower alkanoic acid which is optionally substituted, for example by halogen, for example acetyl, trichloroacetyl or pivaloyl, or the acyl radical of a carbonic acid monoester, especially of a mono-lower alkyl ester, for example ethoxycarbonyl or isobutoxycarbonyl.

The radical $R_4$ in the cephalosporanic acid derivatives of the formula Ib represents, as mentioned, a hydrogen atom (with the side chain in the 3-position of Cephalosporin C missing) or an unsubstituted or substituted methyl group. Substituents of the methyl group are above all a free, esterified or etherified hydroxyl group, an etherified mercapto group, an optionally N-substituted carbamoyloxy or thiocarbamoylmercapto group, a quaternary ammonium group or the nitrile group.

An esterified hydroxyl group contains, as the acid radical, above all the radical of a carboxylic acid or thiocarboxylic acid, for example lower alkanoyl which is optionally substituted by halogen atoms, especially chlorine, such as formyl, propionyl, butyryl, pivaloyl and chloroacetyl, but especially acetyl, or aroyl or aryl-lower alkanoyl which are optionally substituted, for example by lower alkyl, lower alkoxy, halogen or nitro, for example benzoyl or phenylacetyl, and also, as a thiocarboxylic acid radical, especially aroylthio which is optionally substituted as mentioned, above all benzoylthio. Additionally, hydroxyl groups esterified by hydrogen halide acids should be mentioned; the methyl group $R_4$ can therefore be substituted, for example by fluorine, chlorine or bromine.

Etherified hydroxyl groups are described, for example, in Belgian Pat. No. 719,710. Lower alkoxy, such as methoxy, ethoxy and n-propoxy, furanyl and pyranyl should be singled out.

Etherified mercapto groups for example contain, as etherifying radicals, lower alkyl, for example methyl, and also optionally substituted phenyl or heterocyclyl, wherein the substituents can be the same as indicated above for the aromatic and heterocyclic radicals $R_6$. The heterocyclyl radicals preferably have 5–6 ring atoms and contain, as hetero-atoms, nitrogen, optionally in the N-oxidised form, and/or oxygen or sulphur. Examples to be mentioned are 1-oxidised 2-pyridyl, pyrimidyl, pyridazinyl, pyrazinyl, imidazolyl, imidazolidyl, and purinyl. Optionally substituted heterocyclyl radicals of aromatic character with 5 ring atoms, which contain at least 2 nitrogen atoms and furthermore an additional hetero-atom from the group of nitrogen, oxygen and sulphur, should be singled out particularly. Preferred substituents are lower alkyl radicals with 1–5 carbon atoms, such as methyl, ethyl, propyl, isopropyl, n-butyl, isobutyl and tert-butyl, lower alkoxy and lower alkylthio radicals with 1–5 carbon atoms, especially methylthio, cycloalkyl radicals such as cyclopentyl and cyclohexyl, or aryl radicals such as phenyl or substituted phenyl, for example phenyl substituted by one or more nitro groups or halogen atoms or lower alkyl or lower alkoxy groups, or unsubstituted or substituted thienyl, especially thienyl-(2), or thienyl substituted as indicated for phenyl, or optionally mono-substituted or disubstituted amino groups, for example acetylamino, tert.butoxycarbonylamino, tert.-amyloxycarbonylamino and sulphonylamino. As examples of the heterocyclyl radical there should be mentioned: 1H-1,2,3-triazol-5-yl, 1,3,4-triazol-2-yl, 5-methyl-1,3,4-triazol-2-yl, 1H-1,2,4-triazol-5-yl, 1-phenyl-3-methyl-1H-1,2,4-triazol-5-yl, 4,5-dimethyl-4H-1,2,4-triazol-3-yl, 4-phenyl-4H-1,2,4-triazol-3-yl, 1H-tetrazol-5-yl, 1-methyl-1H-tetrazol-5-yl, 1-ethyl-1H-tetrazol-5-yl, 1-n-propyl-1H-tetrazol-5-yl, 1-isopropyl-1H-tetrazol-5-yl, 1-n-butyl-1H-tetrazol-5-yl, 1-cyclopentyl-1H-tetrazol-5-yl, 1-phenyl-1H-tetrazol-5-yl, 1-p-chlorophenyl-1H-tetrazol-5 -yl, 1,2,3-thiadiazol-5-yl, 1,3,4-thiadiazol-2-yl, 1,2,4-thiadiazol-3-yl, 1,2,4-thiadiazol-5-yl, 3-methyl-1,2,4-thiadiazol-5-yl, 2-methyl-1,3,4-thiadiazol-5-yl, 2-methylthio-1,3,4-thiadiazol-5-yl, 2-ethyl-1,3,4-thiadiazol-5-yl, 2-n-propyl-1,3,4-thiadiazol-5-yl, 2-isopropyl-1,3,4-thiadiazol-5-yl, 2-phenyl-1,3,4-thiadiazol-5-yl, 1,2,4-oxadiazol-5-yl, 1,2,3-oxadiazol-5-yl, 1,3,4-oxadiazol-5-yl, 2-methyl-1,3,4-oxadiazol-5-yl, 2-ethyl-1,3,4-oxadiazol-5-yl, 2-phenyl-1,3,4-oxadiazol-5-yl, 2-p-nitrophenyl-1,3,4-oxadiazol-5-yl, 2-[thienyl(2)]-1,3,4-oxadiazol-5-yl and thiatriazol-5-yl.

An optionally N-substituted carbamoyloxy group or thiocarbamoylmercapto group is, for example, a group of the formula $-O-CO-NH-R_{10}$ or

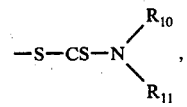

wherein $R_{10}$ is an optionally halogen-substituted lower alkyl radical and $R_{11}$ is hydrogen or $R_{10}$. Above all, $R_{10}$ is methyl, ethyl or chlorine-substituted methyl or ethyl, especially β-chloroethyl.

In a quaternary ammonium-methyl group $R_4$ the ammonium part is preferably a pyridinium group which is optionally substituted, for example by lower alkyl, as mentioned above, or by optionally substituted carboxyl, such as lower alkoxycarbonyl, for example ethoxycarbonyl, or carbamoyl.

Salts of compounds of the present invention are above all pharmaceutically usable non-toxic salts of those compounds which can form salts with bases. Such salts are above all metal salts or ammonium salts, such as alkali metal salts, alkaline earth metal salts and earth metal salts, for example sodium, potassium, magnesium, calcium or aluminium salts, as well as ammonium salts with ammonia or suitable organic bases, in which case it is possible to use for the salt formation above all aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example bicyclohexylamine, or benzylamines, for example N,N'-dibenzylethylenediamine, and also bases of the pyridine type, for example pyridine, collidine or quinoline.

The new compounds can be in the form of mixtures of isomers, for example racemates, or of individual isomers, for example optically active antipodes.

The new compounds of the formula I display a pharmacological action, especially a particularly pronounced anti-bacterial action. Thus they are active against gram-positive bacteria, such as Staphylococcus aureus, but above all against gram-negative bacteria, for example Escheria coli, Klebsiella pneumonia, and Salmonella typhosa, and especially against Bacterium proteus as well as Pseudomonas aeruginosa. Thus they inhibit the growth of Pseudomonas aeruginosa at dilutions down to 0.4 γ/ml. They can therefore be used for combating infections which are caused by such microorganisms, and also be used as fodder additives, for the preservation of foodstuffs or as disinfectants.

Compounds to be singled out are 3-cephem compounds of the formula

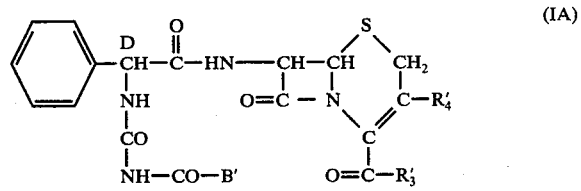

(IA)

and especially penam compounds of the formula

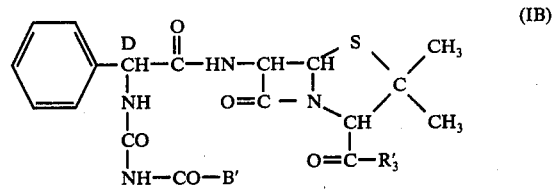

(IB)

wherein $R_3'$ in particular is hydroxyl or lower alkoxy, for example methoxy or tert.-butoxy, 2halogeno-lower alkoxy, for example 2,2,2-trichloroethoxy, 2-bromoethoxy or 2-iodoethoxy, phenacyloxy, phenyl-lower alkoxy, for example benzyloxy or diphenylmethoxy, amino, lower alkylamino, for example methylamino, di-lower alkylamino, for example dimethylamino, or morpholino, and $R_4'$ represents hydrogen, methyl, lower alkanoyloxymethyl, for example acetoxymethyl, pyridiniummethyl, 1-oxydised 2-pyridylthiomethyl, 1,3,4-thiadiazol-2-ylthiomethyl, 2-methyl-1,3,4-thiadiazol-5-ylthiomethyl, 3-methyl-1,2,4-thiadiazol-5-ylthiomethyl or 1-methyl-5-tetrazolylthiomethyl, and wherein B' represents $-S-R_6'$,

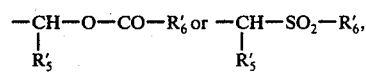

wherein $R_5'$ represents hydrogen, lower alkyl, above all methyl, phenyl, thienyl, furyl or pyridyl and $R_6'$ has the following meanings:

(a) A lower alkyl radical which is optionally substituted by halogen, for example iodine, bromine or fluorine, but especially chlorine, trifluoromethyl, lower alkoxy such as methoxy, aryloxy such as phenoxy or lower alkanoyloxy such as acetoxy, above all methyl, ethyl, isopropyl, chloromethyl, dichloroethyl or phenoxymethyl; or (b) A phenyl, naphthyl or benzyl radical which is optionally substituted by lower alkyl, for example methyl or ethyl, lower alkoxy, for example methoxy or ethoxy, halogen, for example chlorine or fluorine, trifluoromethyl or nitro, for example phenyl, naphthyl, benzyl, p-nitrophenyl or p-tert.butylphenyl, or (c) An optionally substituted monocyclic heterocyclyl radical of aromatic character with 1-2 ring heteroatoms and 5-6 ring atoms or a corresponding heterocyclylmethyl radical wherein the substituents are those mentioned under (b), above all furyl, thienyl, furfuryl, thenyl, pyridyl, pyrazinyl and pyrimidyl.

Penam compounds of the formula IB, wherein B' represents acetoxymethyl, α-acetoxyethyl, α-chloroacetoxy-ethyl, α-phenoxyacetoxy-ethyl, phenylsulphonylmethyl, p-tert.-butylphenylsulphonylmethyl, naphthylsulphonylmethyl or benzylthio, and wherein $R_3'$ represents hydroxy, as well as non-toxic salts such as alkali metal salts, for example sodium salts or potassium salts, or alkaline earth metal salts, such as calcium salts, of these compounds, are therapeutically particularly valuable.

The new compounds are manufactured according to methods which are in themselves known. Thus they can be obtained if (a) a compound of the formula II

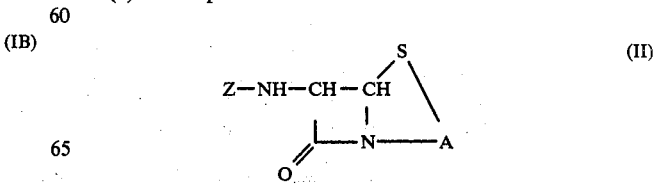

(II)

in which Z represents the radical

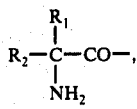

wherein $R_1$, $R_2$ and A have the meaning indicated for the formula I, or a salt thereof, is reacted with an acylisocyanate of the formula III $$O=C=N-CO-B \qquad III$$

wherein B has the meaning indicated for the formula I, or (b) a compound of the formula II, wherein Z represents hydrogen, is N-acylated with an acyl radical of the formula IV

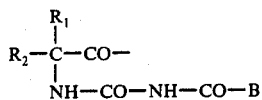 IV wherein B, $R_1$ and $R_2$ have the meaning indicated for the formula I and, if desired, in a resulting compound of the formula Ia or Ib an optionally functionally modified carboxyl group $R_3$ is converted into another $R_3$ group and/or an optionally substituted methyl group $R_4$ is converted into another $R_4$ group and/or, if desired, a compound obtained as the free acid is converted into a salt or a salt obtained is converted into the free acid and/or an isomer mixture obtained is separated into the individual isomers.

In a starting material of the formula II the group $R_3$ in the radical —S A— denotes, for example, one of the abovementioned functionally modified, especially esterified, carboxyl groups, such as a carboxyl group esterified by di-lower alkylhalogenosilyl or tri-lower alkylsilyl, but preferably a free carboxyl group. A N-silylated or N-stannylated derivative of a starting material contains, for example, the abovementioned organic silyl or stannyl radicals, such as tri-lower alkylsilyl, for example trimethylsilyl, bonded to the amino group. Salts of starting compounds of the formula II are, in particular, those of compounds having a free carboxyl group, above all ammonium salts, such as tri-lower alkyl ammonium salts, for example triethyl ammonium salts, and also alkali metal salts.

The reaction of the compound II with the acylisocyanate according to (a) is carried out in a manner which is in itself known. The solvents used are, for example, halogenated, especially chlorinated, hydrocarbons such as methylene chloride, chloroform, carbon tetrachloride, ethylenedichloride or ethylene tetrachloride, or hydrocarbons such as benzene, and also, for example, acetonitrile, tetrahydrofurane, ether or mixtures of these solvents. The reaction is preferably carried out in the presence of a base, for example a tertiary organic nitrogen base such as triethylamine, diisopropylethylamine, N,N-diethylaminoacetic acid ethyl ester, N-ethylmorpholine, N,N-dimethylaniline, pyridine, p-dimethylaminopyridine, collidine or 2,6-lutidine. It is carried out at room temperature or slightly elevated temperature or, preferably, with cooling, for example at temperatures of −40° to +60° C. The acylisocyanates of the formula III are known or can be manufactured in a known manner. Thus, they can be obtained by reaction of acid halides, for example acid chlorides, with silver cyanate. Preferably, they are manufactured according to the process described by A. J. Speciale et al. (J. Org. Chem. 30, 4306 (1965)) by reaction of primary amides of the formula B—CO—NH$_2$, wherein B has the indicated meaning, with oxalyl chloride. The reaction is carried out in an inert solvent, preferably halogenated hydrocarbon such as indicated above. It is conducted with exclusion of moisture, at temperatures of approx. 20°–120° C. The acylisocyanates do not have to be isolated but can, for example, be used in the form of solutions or suspensions in which they are obtained during their manufacture.

The acylation of the compound II according to (b) with the acyl radical IV is carried out according to methods which are in themselves known, especially in the manner known from peptide chemistry for the acylation of weakly basic amino groups. The acylating agent used which contains the acyl radical IV is either the corresponding acid, in which case the reaction is carried out in the presence of a condensation agent, for example a carbodiimide, such as dicyclohexylcarbodiimide, or of Woodward reagent K or L, or a reactive acid derivative, for example an acid halide, especially an acid chloride or bromide, an acid azide, an activated ester or a mixed anhydride, for example an anhydride with a monoesterified carbonic acid such as a carbonic acid lower alkyl ester, for example carbonic acid methyl ester, or with an optionally halogen-substituted lower alkanoic acid such as formic acid, pivalic acid or trichloroacetic acid. Above all, an activated ester is used for the acylation, especially the p-nitrophenyl ester, 2,4-dinitrophenyl ester, 2,4,5- or 2,4,6-trichlorophenyl ester or pentachlorophenyl ester, and also, for example, the cyanomethyl ester, N-hydroxysuccinimide ester, N-hydroxypiperidine ester and N-hydroxyphthalimide ester.

The acylation reaction is carried out in the presence of a solvent or diluent, if desired in the presence of a catalyst and/or in the presence of basic agents such as aliphatic, aromatic or heterocyclic nitrogen bases, for example triethylamine, diisopropylethylamine, N,N-diethylaminoacetic acid ethyl ester, N-ethylmorpholine, N,N-dimethylaniline, pyridine, 2-hydroxypyridine, p-dimethylaminopyridine, collidine and 2,6-lutidine.

The reaction is carried out at room temperature or with cooling or warming, for example at temperatures of −70° to +100° C., if appropriate in an inert gas atmosphere, for example a nitrogen atmosphere and/or with exclusion of moisture.

The acylating agents are known or can be manufactured in a manner which is in itself known.

A derivative which is suitable for introducing the acyl group IV, especially an activated ester, for example of the formula

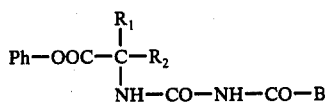

wherein Ph represents a nitro-substituted or halogen-substituted phenyl radical, and B, $R_1$ and $R_2$ have the abovementioned meaning can be obtained, for example, by reaction of the ester

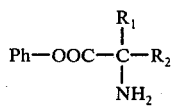

with the acylisocyanate $B - CO - N = C = O$.

In the reaction (a) or (b), free hydroxyl, mercapto, amino and/or carboxyl groups which may be present in the reactants are appropriately protected, especially by protective groups which can easily be split off, such as are known, for example, from the synthesis of peptides, compare Schröder and Lübke "The Peptides", Vol. I, Academic Press, New York and London, 1965, and Th. Wieland, Angew. Chem. 63 (1951) 7–14, 66 (1954), 507–512, 69 (1957), 362–372, 71 (1959), 417–425 and 75 (1963), 539–551. As amino-protective groups there should be mentioned, for example, optionally substituted aralkyl groups such as diphenylmethyl or triphenylmethyl groups, or acyl groups such as formyl, trifluoroacetyl, phthaloyl, p-toluenesulphonyl, benzylsulphonyl, benzenesulphenyl or o-nitrophenylsulphenyl, or above all groups which are derived from carbonic acid or thiocarbonic acid, such as carbobenzoxy groups which are optionally substituted in the aromatic radical by halogen atoms, nitro groups, lower alkyl or lower alkoxy or lower carbalkoxy groups, for example carbobenzoxy, p-bromocarbobenzoxy or p-chlorocarbobenzoxy, p-nitrocarbobenzoxy and p-methoxycarbobenzoxy, coloured benzyloxycarbonyl groups such as p-phenylazo-benzyloxycarbonyl and p-(p'-methoxyphenylazo)-benzyloxycarbonyl, tolyloxycarbonyl, 2-phenyl-isopropoxycarbonyl, 2-tolyl-isopropoxycarbonyl and above all 2-(para-biphenylyl)-2-propoxycarbonyl, and also aliphatic oxycarbonyl groups such as, for example, allyloxycarbonyl, cyclopentyloxycarbonyl, tert.amyloxycarbonyl, adamantyloxycarbonyl, 2,2,2-trichloroethoxycarbonyl, 2-iodoethoxycarbonyl and above all tert.butoxycarbonyl, and also, for example, carbamoyl, thiocarbamoyl, N-phenylcarbamoyl and N-phenylthiocarbamoyl. Ester groups for protecting a free carboxyl group, which can easily be split off, have already been listed above. Hydroxyl groups are preferably protected by etherification, for example with tert-.butanol. Trityl, for example, is suitable as the mercapto protective group.

In a compound of the formula I obtained according to the invention, a protected carboxyl group $R_3$, especially an esterified carboxyl group which can easily be converted into the free carboxyl group, can be converted in the abovementioned manner into the free carboxyl group. It is also possible, before splitting off the ester group, to convert the ester group into another ester group, for example to convert a 2-bromoethyl ester group into a 2-iodoethyl ester group.

In a compound of the formula I obtained according to the process or a compound of the formula II used as the starting material, wherein $R_3$ represents a free carboxyl group, the latter can be converted in a manner which is in itself known into a protected carboxyl group, especially a functionally modified carboxyl group. Thus, a free carboxyl group can be esterified, for example by treatment with a diazo compound, such as a diazo-lower alkane, for example diazo-methane or diazoethane, or a phenyl-diazo-lower alkane, for example phenyl-diazomethane or diphenyldiazomethane, or by reaction with an alcohol suitable for esterification, in the presence of an esterifying agent, such as a carbodiimide, for example dicyclohexylcarbodiimide, as well as carbonyldiimidazole, or in accordance with any other known and suitable esterification process, such as the reaction of a salt of the acid with a reactive ester of an alcohol with a strong inorganic acid or with a strong organic sulphonic acid. Furthermore, acid halides, such as acid chlorides (manufactured, for example, by treatment with oxalyl chloride), activated esters (formed, for example, with N-hydroxy-nitrogen compounds) or mixed anhydrides (obtained, for example, with halogenoformic acid lower alkyl esters, such as chloroformic acid ethyl ester, or with halogenoacetic acid halides, such as trichloroacetic acid chloride) can be converted into an esterified carboxyl group by reaction with alcohols, optionally in the presence of a base, such as pyridine, and furthermore a mixed anhydride with a carbonic acid half ester can be converted into an esterified carboxyl group by splitting off carbon dioxide.

Carboxyl groups esterified by organic silyl or stannyl groups can be formed in a manner which is in itself known, for example by treating compounds of the formula I or II, wherein $R_3$ represents a free carboxyl group, or salts, such as alkali metal salts, for example sodium salts, thereof, with a suitable silylating agent, such as a di-lower alkyl-dihalogenosilane, for example dimethyldichlorosilane, a tri-lower alkylsilyl halide, for example trimethyl-silyl chloride, or an optionally N-mono-lower alkylated, N,N-di-lower alkylated, N-tri-lower alkylsilylated or N-lower alkyl-N-tri-lower alkylsilylated N-(tri-lower alkylsilyl)-amine (see, for example, British Pat. No. 1,073,530) or with a suitable stannylating agent, such as bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or a tri-lower alkyl-tin halide, for example tri-n-butyl-tin chloride (see, for example, Netherlands published specification No. 67/17,107).

Mixed anhydrides of compounds of the formula I or II, wherein $R_3$ represents a free carboxyl group, can be manufactured by reacting such a compound or preferably a salt thereof, especially an alkali metal salt or ammonium salt thereof, with a reactive derivative, such as a halide, for example the chloride, of an acid, for example a halogenoformic acid lower alkyl ester or a lower alkanecarboxylic acid chloride.

A resulting compound of the formula I, wherein the group $R_3$ represents a free carboxyl group, can be converted into the corresponding amide in a manner which is in itself known. Thus it is possible, for example, to treat the acid or a corresponding acid halide or mixed anhydride or a corresponding ester, especially an activated ester, but also, for example, a lower alkyl ester, such as the methyl ester or ethyl ester, with ammonia or a primary or secondary amine, and when using the acid a suitable condensation agent, such as a carbodiimide, for example dicyclohexylcarbodiimide, is used. It is also possible to react the free carboxylic acid with an isocyanate which is derived from the corresponding amine and to convert the mixed anhydride formed into the desired amine, whilst splitting off carbon dioxide.

In compounds of the formula I, wherein the fragment —S—A— represents the group of the formula Ib, a radical $R_4$ can be converted into another group of this nature. Thus it is possible to treat a compound having an esterified hydroxy-methyl radical $R_4$, wherein the esterified hydroxyl group especially denotes lower alkanoyloxy, for example acetoxy, with pyridine at an elevated temperature, or first to react it with thiobenzoic acid and then to treat it with pyridine in the presence of a mercury salt, or to react it with a suitable salt, such as potassium thiocyanate, potassium iodide or potassium nitrate, and with pyridine in the presence od water at a pH value of about 6.5 which is set up, for example, with the aid of phosphoric acid, and thus to obtain the corresponding pyridiniummethyl compound which can, if required, be converted into the internal salt (zwitter-ion form), for example by treatment with a suitable ion exchange reagent. Furthermore it is possible to react compounds having a lower alkanoyloxymethyl group, for example acetoxymethyl group, as the radical $R_4$, with a mercapto compound, such as an optionally substituted lower alkylmercaptan, phenylmercaptan or heterocyclomercaptan, and thus to obtain compounds of the formula I, wherein $R_4$ in a partial formula Ib represents an etherified mercapto group.

Salts of compounds of the formula I can be manufactured in a manner which is in itself known. Thus it is possible to form salts of compounds of the formula I, wherein $R_3$ represents a free carboxyl group, for example by treatment with metal compounds, such as alkali metal salts of suitable carboxylic acids, for example the sodium salt of α-ethyl-caproic acid, or with ammonia or a suitable organic amine.

Salts can be converted in the usual manner into the free compounds, metal and ammonium salts being converted, for example, by treatment with suitable acids or ion exchangers.

Resulting mixtures of isomers can be separated into the individual isomers according to methods which are in themselves known, for example by fractional crystallisation, adsorption chromatography (column chromatography or thin layer chromatography) or other suitable methods of separation. Resulting racemates can be separated into the antipodes in the customary manner, if necesary after introduction of suitable salt-forming groupings, for example by forming a mixture of diastereoisomeric salts with optically active salt-forming agents, separating a mixture into the diastereoisomeric salts and converting the separated salts into the free compounds, or by fractional crystallisation from optically active solvents.

The process also encompasses those embodiments according to which compounds which arise as intermediate producte are used as starting substances and the remaining process steps are carried out with these, or the process is stopped at any stage; furthermore, starting substances can be used in the form of derivatives or be formed during the reaction.

Preferably, such starting substances are used, and the reaction conditions are so chosen, that the compounds initially listed as being particularly preferred are obtained.

The starting substances of the formula II are known or can be manufactured according to the processes already mentioned.

The new compounds can be used as medicines, for example in the form pharmaceutical preparations which contain an effective amount of the active substance together with, or mixed with inorganic or organic, solid or liquid, pharmaceutically usable excipients which are suitable for enteral or, preferably, parenteral administration. Thus, tablets or gelatine capsules are used which contain the active substance together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also containing binders, for example magnesium aluminium silicate, starches, such as corn starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Preferably, the pharmacologically active compounds of the present invention are used in the form of injectable, for example intravenously administerable, preparations, or of infusion solutions. Such solutions are preferably isotonic aqueous solutions or suspensions which can, for example, be manufactured before use from lyophilised preparations which contain the active substance alone or together with an excipient, for example mannitol. The pharmaceutical preparations can be sterilised and/or contain auxiliary substances, for example preservatives, stabilisers, wetting agents and/or emulsifiers, solubilising agents, salts for regulating the osmotic pressure and/or buffers. The present pharmaceutical preparations which can, if desired, contain further pharmacologically valuable substances, are manufactured in a manner which is in itself known, for example by means of conventional mixing, granulating, dragée-making, dissolving or lyophilising processes, and contain from about 0.1 to 100%, especially from about 1% to about 50%, of lyophilisates or up to 100% of the active substance.

In the context of the present description, organic radicals described as "lower" contain up to 6, preferably up to 4, carbon atoms; acyl radicals contain up to 20, preferably up to 12, carbon atoms.

The examples which follow serve to illustrate the invention.

The following systems are used in thin layer chromatography:
System
52A n-butanol-glacial acetic acid-water (67:10:23)
67 n-butanol-ethanol-water (40:10:50, upper phase)
101 n-butanol-pyridine-glacial acetic acid-water (38:24:8:30)
101A n-butanol-pyridine-glacial acetic acid-water (42:24:4:30).

In the Examples, "MIC" means the minimum inhibitory concentration in γ/ml which is measured by the gradient plate test described in "Antibiotics" Vol. I by Gottlieb and Shaw, New York, 1967, page 508, a modified method of that described by V. Bryson and R. Szybalski, Science 116, 45 (1952). The MIC is determined on strains of *Pseudomonas aeruginosa* (*Ps.aer.*) ATCC 12055, *Ps.aer.* ATCC 10145, Ps.aer. Prof. Richmond, *Pseudomonas aer.* 313, *Staphylococcus aureus* (*St.aur.*) Smith 14, *Escherichia coli* (*E.coli*) ATCC 2018, *E.coli* 205, *Klebsiella pneumoniae* (*K.pn.*)327 and/or *Salmonella typhimurium* (*S.typh.*) 277.

EXAMPLE 1

A suspension of 1.70 g of anhydrous 6-(D-α-phenylglycylamino)-penicillanic acid in 30 ml of methylene chloride is mixed at room temperature, whilst stirring and excluding moisture, with 1.05 ml of triethylamine and then cooled to −10° C. Thereafter a solution of 1.07 g of acetoxyacetylisocyanate (manufactured according to the method of A. J. Speziale et al, J. org. Chem. 30, 4306 (1965)) in 10 ml of methylene chloride is added dropwise over the course of 5 minutes to the clear solution at −10° C., whilst stirring and cooling. Care is taken that the internal temperature does not exceed 0° C. The reaction mixture is stirred for 1 hour at 0° C. and is subsequently extracted with 70 ml of phosphate buffer solution of pH 7.5. The phosphate buffer solution is twice extracted with ethyl acetate and the aqueous phase is then covered with ethyl acetate, rendered acid (pH 2.5) by adding 20% strength phosphoric acid whilst stirring and cooling at 10° C. by means of an ice bath, and extracted three times with ethyl acetate. The ethyl acetate extracts are combined, twice washed with 50 ml portions of sodium chloride solution and dried over sodium sulphate, and the solvent is evaporated off on a rotary evaporator at 45° C. The product which remains is purified by precipitation from petroleum ether. 6-[D(−)-α(3-Acetoxyacetyl-1-ureido)-phenylacetamido]phenicillanic acid melts at: 151°–155° C. (with decomposition).

Thin layer chromatogram on silica gel: $Rf_{52A} = 0.62$, $Rf_{101} = 0.60$, $Rf_{67} = 0.23$, $Rf_{101A} = 0.55$. $[\alpha]_D^{20} = +166° \pm 1°$ (c = 1.00 in 0.5 N NaHCO$_3$). MIC: Ps.aer. 12055 = 10; Ps.aer. 10145 = 30; Ps.aer. 313 = 30; St.aur. 14 = 1; E.coli 2018 = 4; Kl.pn. 327 = 50; S.typh. 277 = 40;

Manufacture of the acetoxyacetylisocyanate:

18.70 g of 2-(acetoxy)-acetamide are dissolved in 80 ml of 1,1,2-trichloroethane, 17.0 ml of oxalyl chloride are then allowed to run in at room temperature whilst stirring and the reaction mixture is boiled for 2.5 hours under reflux. Thereafter the dark solution is cooled and fractionated at 50 mm Hg. Acetoxyacetylisocyanate boils at 100°–103° C./50 mm Hg.

EXAMPLE 2

6-[D(−)-α-(3-Phenylsulphonylacetyl-1-ureido)-phenylacetamido]-penicillanic acid is obtained by reaction of 3.0 g of anhydrous 6-(D-α-phenylglycylamino)-penicillanic acid in 40 ml of methylene chloride, in the presence of 1.80 ml of triethylamine, with a solution of 2.10 g of phenylsulphonylacetylisocyanate in 15 ml of methylene chloride, as in Example 1. The crude product (4.0 g, 81% of theory) is purified by filtration over a 40-fold amount of silica gel, using ethyl acetate as the solvent, and subsequently by precipitation from ethyl acetate solution by means of a mixture of ether and petroleum ether.

Melting point: 159°–161° C., with decomposition.

Thin layer chromatogram on silica gel: $Rf_{52} = 0.56$, $Rf_{101} = 0.60$, $Rf_{67} = 0.31$, $Rf_{101A} = 0.54$. $[\alpha]_D^{20} = +136° \pm 1°$ (c = 0.810 in dimethylsulphoxide).

Manufacture of phenylsulphonylacetylisocyanate:

11.90 g of 2-(phenylsulphonyl)-acetamide are suspended in 100 ml of ethylene chloride, 7.70 ml of oxalyl chloride are then allowed to run into the suspension at room temperature whilst stirring, and the reaction mixture is boiled for 5 hours under reflux. After evaporating off the solvent on a rotary evaporator at 60° C., the residual oil is fractionated at 0.8 mm Hg. During the entire reaction time, dry nitrogen is passed through the reaction mixture. Phenylsulphonylacetylisocyanate boils at 160°–166° C./0.8 mm Hg.

EXAMPLE 3

6-[D(−)-α(3-L(+)-α-Acetoxy-propionyl-1-ureido)-phenylacetamido]-penicillanic acid is obtained by reaction of 20.0 g of anhydrous 6-(D-α-phenylglycylamino)-penicillanic acid in 300 ml of methylene chloride, in the presence of 12.20 ml of triethylamine, with a solution of 11.00 g of L(+)-α-acetoxypropionylisocyanate in 70 ml of methylene chloride, as in Example 1.

The crude product (24.8 g, 85% of theory) is chromatographed on a 30-fold amount of silica gel. The fractions eluted with a mixture of methylene chloride and methyl acetate (1:1) as the solvent are combined, the solvent is evaporated off on a rotary evaporator at 40° C. and the residual foam is purified by precipitation from ethyl acetate solution by means of a mixture of ether and petroleum ether.

Melting point: 149°–152° C., with decomposition.

Thin layer chromatogram on silica gel: $Rf_{52A} = 0.70$, $Rf_{101} = 0.67$, $Rf_{67} = 0.45$, $Rf_{101A} = 0.61$. $[\alpha]_D^{20} = +138° \pm 1°$ (c = 1.030 in 0.5 N NaHCO$_3$).

Manufacture of L(+)-α-acetoxypropionylisocyanate:

15.0 g of L(+)-acetyl-lactic acid amide are dissolved in 60 ml of 1,1,2-trichloroethane, 12.80 ml of oxalyl chloride are then allowed to run in at room temperature whilst stirring and the reaction mixture is boiled under reflux for 5 hours. Thereafter the dark solution is fractionated at 50° mm Hg. During the entire reaction time, dry nitrogen is passed through the reaction mixture. L(+)-α-Acetoxypropionylisocyanate boils at 95°–97° C./50 mm Hg.

EXAMPLE 4

6-[D(−)-α-(3-α-Acetoxy-phenylacetyl-1-ureido)-phenylacetamido]-penicillanic acid is obtained by reaction of 3.49 g of anhydrous 6-(α-phenylglycylamino)-penicillanic acid in 70 ml of methylene chloride, in the presence of 2.10 ml of triethylamine, with a solution of 3.28 g of α-acetoxyphenylacetylisocyanate in 50 ml of tetrahydrofurane as in Example 1. The crude product (3.9 g, 70% of theory) is purified by precipitation from ethyl acetate solution with a mixture of ether and petroleum ether. Melting point: 157°–160° C., with decomposition. Thin layer chromatogram on silica gel: $Rf_{52A} = 0.63$, $Rf_{101} = 0.60$, $Rf_{67} = 0.35$, $Rf_{101A} = 0.57$. $[\alpha]_D^{20} = +164° \pm 1°$ (c = 1.154 in dimethylsulphoxide).

Manufacture of α-acetoxyphenylacetylisocyanate:

13.50 g of acetylmandelic acid amide are dissolved in 60 ml of 1,1,2-trichloroethane, 9.0 ml of oxalyl chloride are then allowed to run in at room temperature whilst stirring and the reaction mixture is boiled for 5 hours under reflux. Thereafter the solvent is evaporated off on a rotary evaporator at 60° C. and the residual oil is fractionated at 0.2 mm Hg. During the entire reaction time, dry nitrogen is passed through the reaction mixture. α-Acetoxyphenylacetylisocyanate boils at 98°–100° C./0.2 mm Hg.

EXAMPLE 5

7-[D(−)-α-(3-Acetoxyacetyl-1-ureido)-phenylacetamido]-cephalosporanic acid is obtained by reaction of 1.80 g of D(−)-cephaloglycine in 300 ml of methylene chloride, in the presence of 0.91 ml of triethylamine, with a solution of 0.93 g of acetoxyacetylisocyanate in 10 ml of methylene chloride, as in Example 1. The crude product (2.2 g, 89% of theory) is purified by crystallisation from a mixture of tetrahydrofurane and ethyl acetate. Melting point: 182°–185° C., with decomposition.

Thin layer chromatogram on silica gel: $Rf_{52A} = 0.33$, $Rf_{101} = 0.59$, $Rf_{67} = 0.23$, $Rf_{101A} = 0.55$. $[\alpha]_D^{20} = +56° \pm 1°$ (c = 1.027 in dimethylsulphoxide).

EXAMPLE 6

Following the procedure of Example 1, 6-[D-(−)-α-(3-p-tert.-butylphenylsulphonylacetyl-1-ureido)-phenylacetamido]-penicillanic acid is obtained by reaction of 6-(D-α-phenylglycylamino)-penicillanic acid with p-tert.butylphenylsulphonylacetyl-isocyanate (boiling point 174°–176° C./1 mm Hg). Melting point 163°–165° C.$[\alpha]_D^{20} = +158° \pm 1°$ (c = 0.784 in dimethylsulphoxide). $Rf_{52A} = 0.72$; $Rf_{67} = 0.44$; $Rf_{101} = 0.63$; $Rf_{101A} = 0.68$. MIC: Ps.aer. 12055 = 15; Ps.aer.10145 = 15; Ps.aer. Richm. = 2; Ps.aer. 313 = 30; St.aur. 14 = 0,3; E.coli 2018 = 20; E.coli 205 = 20; K.pn.327 = 35; S.typh.277 = 30.

EXAMPLE 7

Following the procedure of Example 1, 6-[D-(−)-α-(3-L(+)-α-butyryloxy-propionyl-1-ureido)-phenylacetamido]-penicillanic acid is obtained by reaction of 6-(D-α-phenylglycylamino)-pencillanic acid with L(+)-α-butyryloxy-propionylisocyanate (boiling point 90°–92° C./13 mm Hg). Melting point 125°–130° C. $[\alpha]_D^{20} = +108° \pm 1°$ (c = 1.166 in dimethylsulphoxide). $Rf_{52A} = 0.66$; $Rf_{67} = 0.42$ $Rf_{101} = 0.61$; $Rf_{101A} = 0.63$

EXAMPLE 8

Following the procedure of Example 1, 6-[D-(−)-α-(3-L(+)-α-(2-furoyloxy)-propionyl-1-ureido)-phenylacetamido]penicillanic acid is obtained by reaction of 6-(D-α-phenylglycylamino)-penicillanic acid with L(+)-α-(2-furoyloxy)propionyl-isocyanate (boiling point 99°–100° C./0.8 mm Hg). Melting point 148°–152° C.$[\alpha]_D^{20} = +221° \pm 1°$ (c = 1.176 in dimethylsulphoxide). $Rf_{52A} = 0.78$; $Rf_{67} = 0.45$; $Rf_{101} = 0.70$; $Rf_{101A} = 0.55$.

EXAMPLE 9

Following the procedure of Example 1, 6-[D-(−)-α-(3-L(+)-α-(2-thenoyloxy)-propionyl-1-ureido)-pencillanic acid is obtained by reaction of 6-(D-α-phenylglycylamino)-penicillanic acid with L(+)-α-(2-thenoyloxy)-propionyl-isocyanate (boiling point 120°–121° C./1 mm Hg). Melting point 160°–163° C.$[\alpha]_D^{20} = +220° \pm 1°$ (c = 1.063 in dimethylsulphoxide). $Rf_{52A} = 0.79$; $Rf_{67} = 0.43$; $Rf_{101} = 0.70$; $Rf_{101A} = 0.55$. MIC: Ps.aer. 12055 = 10; Ps.aer. 10145 = 10; Ps.aer.Richm. = 2; Ps.aer.313 = 10; St.aur.14 = 0.35; E.coli 2018 = 5; E.coli 205 = 4; K.pn.327 = 30; S.typh.277 = 20.

EXAMPLE 10

Following the procedure of Example 1, 6-[D-(−)-α-[3-D,L-α-acetoxy-(2-furylacetyl)-1-ureido]-phenylacetamido]-penicillanic acid is obtained by reaction of 6-(D-α-phenylglycylamino)-penicillanic acid with D,L-α-acetoxy-2-furylacetyl-isocyanate (boiling point 95°–97° C./1 mm Hg). Melting point 152°–153° C. $[\alpha]_D^{20} = +150° \pm 1°$ (c = 1.079 in dimethylsulphoxide). $Rf_{52A} = 0.64$; $Rf_{67} = 0.33$; $Rf_{101} = 0.57$; $Rf_{101A} = 0.62$.

EXAMPLE 11

Following the procedure of Example 1, 6-[D-(−)-α-[3-D,L-α-acetoxy-(2-theinylacetyl)-1-ureido]-phenylacetamido]penicillanic acid is obtained by reaction of 6-(D-α-phenylglycylamino)-penicillanic acid with D,L-α-acetoxy-2-thienylacetyl-isocyanate (boiling point 113°–115° C./1 mm Hg). Melting point 150°–155° C. $[\alpha]_D^{20} = +148° \pm 1°$ (c = 1.014 in dimethylsulphoxide). $Rf_{52A} = 0.67$; $Rf_{67} = 0.32$; $Rf_{101} = 0.61$; $Rf_{101A} = 0.60$.

EXAMPLE 12

Following the procedure of Example 1, 6-[D-(−)-α-(3-L(+)-α-(p-nitrobenzoyloxy)-propionyl-1-ureido)-phenylacetamido]-penicillanic acid is obtained by reaction of 6-(D-α-phenylglycylamino)-penicillanic acid with L(+)-α-(p-nitrobenzoyloxy)-propionyl-isocyanate (boiling point 177°–178° C./1 mm Hg). Melting point 160°–170° C. $[\alpha]_D^{20} = \pm 1°$ (c = 1.044 in dimethylsulphoxide). $Rf_{52A} = 0.72$; $Rf_{67} = 0.67$; $Rf_{101} = 0.63$; $Rf_{101A} = 0.64$.

EXAMPLE 13

Following the procedure of Example 1, 6-[D(−)-α-(3-L(+)-α-chloroacetoxy-propionyl-1-ureido)-phenylacetamido]-penicillanic acid is obtained by reaction of 6-(D-α-phenylglycylamino)-penicillanic acid with L-(+)-α-chloroacetoxypropionyl-isocyanate (boiling point 113°–114° C./15 mm Hg). Melting point 125°–130° C. $[\alpha]_D^{20} = 110° \pm 1°$ (c = 0.996 in dimethylsulphoxide). $Rf_{52A} = 0.68$; $Rf_{67}$ 32 0.35; $Rf_{101} = 0.56$; $Rf_{101A} = 0.54$. MIC: Ps.aer.12055 = 10; Ps.aer.10145 = 10; Ps.aer.Richm. = 3; Ps.aer.313 = 30; St.aur.14 = 0.3; E.coli 2018 = 4; E.coli 205 = 10; S.typh.277 = 10.

EXAMPLE 14

Following the procedure of Example 1, 6-[D-(−)-α-(3-L(+)-α-phenoxyacetoxy-propionyl-1-ureido)-phenylacetamido]penicillanic acid is obtained by reaction of 6-(D-α-phenylglycylamino)-penicillanic acid with L-(+)-α-phenoxyacetoxypropionyl-isocyanate (boiling point 135°–136° C./0.8 mm Hg; melting point 27°–29° C.). Melting point 135°–140° C. $[\alpha]_D^{20} = +134°$ (c = 1.226 in dimethylsulphoxide). $Rf_{52A} = 0.70$; $Rf_{67} = 0.42$; $Rf_{101} = 0.59$; $Rf_{101A} = 0.61$. MIC: Ps.aer.12055 = 10; Ps.aer.10145 = 10; Ps.aer.Richm. = 2; Ps.aer.313 = 30; St.aur.14 = 0.06; E.coli 2018 = 3; E.coli 205 = 5; K.pn.327 = 20; S. typh.277 = 6.

EXAMPLE 15

Following the procedure of Example 1, 6-[D(−)-α-(3-n-propylmercaptocarbonyl-1-ureido)-phenylacetmido]-penicillanic acid is obtained by reaction of 6-(D-α-phenylglyclyamino)-penicillanic acid with n-propylmercaptocarbonylisocyanate (boiling point 95°–97° C./60 mm Hg). Melting point 147°–149° C. $[\alpha]_D^{20} = +196° \pm 1°$ (c = 1.160 in dimethylsulphoxide). $Rf_{52A} = 0.70$; $Rf_{67} = 0.45$; $Rf_{101} = 0.65$; $Rf_{101A} = 0.61$.

EXAMPLE 16

Following the procedure of Example 1, 6-[D(−)-α-(3-benzylmercaptocarbonyl-1-ureido)-phenylacetamido]-penicillanic acid is obtained by reaction of 6-(D-α-phenylglycylamino)-penicillanic acid with benzylmercaptocarbonylisocyanate (boiling point 99°–100° C./2 mm Hg). Melting point 140°–145° C. $[\alpha]_D^{20} = +197°$ (c = 0.956 in dimethylsulphoxide). $Rf_{52A} = 0.68$; $Rf_{67} = 0.43$; $Rf_{101} = 0.60$; $Rf_{101A} = 0.59$. MIC: Ps.aer.12055 = 6; Ps.aer.10145 = 6; Ps.aer.Richm. = 4; Ps.aer.313 = 20; St.aur.14 = 0.5; E.coli 2018 = 4; E.coli 205 = 5; K.pn.327 = 50; S.typh. 277 = 25.

EXAMPLE 17

Following the procedure of Example 1, 6-[D(−)-α-(3-p-chlorophenylsulphonylacetyl-1-ureido)- phenylacetamido]-penicillanic acid is obtained by reaction of 6-(D-α-phenylglycylamino)-penicillanic acid with p-chlorophenylsulphonylacetyl-isocyanate (boiling point 174°-176° C./1 mm Hg; melting point 58°-60° C.). Melting point 158°-161° C. $[α]_D^{20} = +146°$ (c = 0.983 in dimethylsulphoxide). $Rf_{524} = 0.68$; $Rf_{67} = 0.38$; $Rf_{101} = 0.59$; $Rf_{1014} = 0.52$. MIC: Ps.aer.12055 = 10; Ps.aer.10145 = 20; Ps.aer. Richm. = 1.5; Ps.aer. 313 = 20; St.aur. 14 = 0.15; E.coli 2018 = 4; E.coli 205 = 4; K.pn.327 = 20; S.typh.277 = 20.

EXAMPLE 18

Following the procedure of Example 1, 6-[D(−)-α-(3-β'-naphthylsulphonylcetyl-1-ureido)-phenylacetamido]penicillanic acid is obtained by reaction of 6-(D-α-phenylglycylamino)-penicillanic acid with β-naphthylsulphonylcetyl-isocyanate (melting point 160°-164° C., from dichloroethylene). Melting point 152°-155° C. $[α]_D^{20} = +110°$ (c = 0.902 in dimethylsulphoxide). $Rf_{524} = 0.73$; $Rf_{67} = 0.40$; $Rf_{101} = 0.61$. MIC: Ps.aer.12055 = 20; Ps.aer. 10145 = 20; Ps.aer.Richm. = 2; Ps.aer.313 = 25; St.aur. 14 = 0.2; E.coli 2018 = 5.5; E.coli 205 = 6.5; K.pn. 327 = 25; K.pn.277 = 20.

What we claim is:

1. A compound of the formula

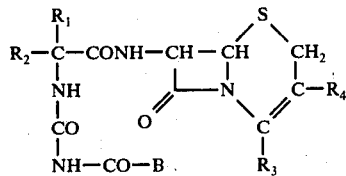

wherein $R_4$ denotes methyl, or methyl mono-substituted by hydroxy, lower alkanoyloxy with up to 6 carbon atoms or a nitrile group, $R_3$ denotes a carboxyl group, $R_1$ is hydrogen and $R_2$ is phenyl, thienyl or furyl and wherein B denotes a group of the formula

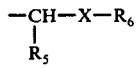

wherein X represents carbonyloxy or sulphonyl, $R_5$ represents hydrogen, lower alkyl, phenyl, thienyl, furyl or pyridyl and $R_6$ represents (a) lower alkyl or lower alkyl mono-substituted by halogen, lower alkoxy, phenoxy or lower alkanoloxy or (b) phenyl, naphthyl, benzyl, furyl, thienyl, furfuryl, thenyl, pyridyl, pyrazinyl or pyrimidyl or phenyl, naphthyl, benzyl, furyl, thienyl, furfuryl, thenyl, pyridyl, pyrazinyl or pyrimidyl mono substituted by lower alkyl, lower alkoxy, halogen or nitro, or a pharmaceutically acceptable salt thereof.

2. The compound of claim 1, wherein $R_3$ denotes a carboxyl group and $R_4$ denotes lower alkanoyloxymethyl with up to 6 carbon atoms and wherein $R_1$ represents hydrogen, $R_2$ represents phenyl, thienyl-(2) or furyl-(2) and B has the meaning indicated in claim 1, or a pharmaceutically acceptable salt thereof.

3. The compound of claim 1, wherein $R_3$ denotes a carboxyl group and $R_4$ denotes acetoxymethyl, $R_1$ represents hydrogen and $R_2$ represents phenyl and B represents

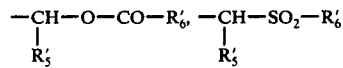

and wherein $R_5'$ represents hydrogen, lower alkyl, phenyl, thienyl, furyl or pyridyl and $R_6'$ represents (a) lower alkl or lower alkyl mono-substituted by halogen, lower alkoxy, phenoxy or lower alkanoyloxy or (b) phenyl, naphthyl, benzyl, furyl, thienyl, furfuryl, thenyl, pyridyl, pyrazinyl or pyrimidyl or phenyl, naphthyl, benzyl, furyl, thienyl, furfuryl, thenyl, pyridyl, pyrazinyl or pyrimidyl mono-substituted by lower alkyl, lower alkoxy, halogen or nitro, or a pharmaceutically acceptable salt thereof.

4. The compound of claim 1, wherein $R_3$ denotes a carboxyl group and $R_4$ denotes acetoxymethyl, $R_1$ represents hydrogen and $R_2$ represents phenyl and B denotes lower alkanoyloxymethyl, α-lower alkanoyloxyethyl or α-lower alkanoyloxybenzyl, or a therapeutically acceptable salt thereof.

5. The compound of claim 1, wherein $R_3$ denotes a carboxyl group and $R_4$ denotes acetoxymethyl, $R_1$ represents hydrogen and $R_2$ represents phenyl and B denotes phenylsulphonylmethyl or naphthylsulphonylmethyl, or a pharmaceutically acceptable salt thereof.

6. A compound as claimed in claim 1, which is 7-[D(−)-α-(3-Acetoxyacetyl-1-ureido)-phenylacetamido]cephalosporanic acid or a pharmaceutically acceptable salt thereof.

7. A pharmaceutical preparation with antibacterial activity which comprises a therapeutically effective amount of a compound of claim 1, or a pharmaceutically acceptable salt thereof, together with a pharmaceutically acceptable carrier.

* * * * *